United States Patent [19]

Schönafinger et al.

[11] Patent Number: 4,845,091

[45] Date of Patent: Jul. 4, 1989

[54] SUBSTITUTED 3-AMINO-SYDNONIMINES, THEIR USE AND PHARMACEUTICAL PRODUCTS CONTAINING THEM

[75] Inventors: Karl Schönafinger, Alzenau; Rudi Beyerle, Frankfurt am Main, Fed. Rep. of Germany; Helmut Bohn; Melitta Just, both of Schöneck; Piero Martorana, Bad Homburg; Rolf-Eberhard Nitz, Frankfurt am Main, all of Fed. Rep. of Germany

[73] Assignee: Cassella Aktiengesellschaft, Frankfurt, Fed. Rep. of Germany

[21] Appl. No.: 885,081

[22] Filed: Jul. 14, 1986

[30] Foreign Application Priority Data

Jul. 20, 1985 [DE] Fed. Rep. of Germany ....... 3526068

[51] Int. Cl.$^4$ ............... A61K 31/41; A61K 31/535; C07D 271/04; C07D 413/04
[52] U.S. Cl. ............................... 514/212; 514/227.9; 514/236.5; 514/252; 514/326; 514/364; 514/227.8; 540/603; 644/58.2; 644/58.7; 644/367; 546/210; 548/125
[58] Field of Search .................. 548/125; 540/603; 544/58.2, 58.7, 367; 546/210; 514/212, 222, 234, 252, 326, 364, 227.8, 236.5

[56] References Cited

U.S. PATENT DOCUMENTS

| | | | |
|---|---|---|---|
| 3,812,128 | 5/1974 | Masuda et al. | 548/125 X |
| 3,833,580 | 9/1974 | Gotz et al. | 548/125 X |
| 4,430,342 | 2/1984 | Hidaka et al. | 548/125 X |
| 4,436,743 | 3/1984 | Schönafinger et al. | 548/125 X |

Primary Examiner—Richard L. Raymond
Attorney, Agent, or Firm—Perman & Green

[57] ABSTRACT

Optically active substituted 3-aminosydnonimines of the general formula I

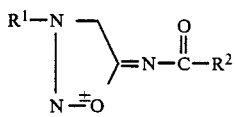

and their pharmacologically acceptable acid addition salts, wherein
$R^1$ denotes, for example, the radical $R^3(R^4)N$-,
$R^2$ denotes the radical 1-methoxyethyl (—CH(CH$_3$)OCH$_3$), acetoxy-phenyl-methyl (—CH(C$_6$H$_5$)O—COCH$_3$), 1-(ethoxycarbonyl)-ethoxy (—O—CH$_3$)CO$_2$C$_2$H$_5$),
$R^3$ denotes alkyl(C$_1$–C$_4$) and
$R^4$ denotes for example alkyl(C$_1$–C$_4$),
possess valuable pharmaceutical properties.

8 Claims, No Drawings

SUBSTITUTED 3-AMINO-SYDNONIMINES, THEIR USE AND PHARMACEUTICAL PRODUCTS CONTAINING THEM

The invention relates to substituted 3-aminosydnonimines of the general formula I

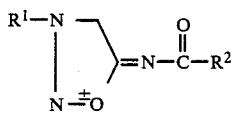  (I)

in optically active form, and their pharmacologically acceptable acid addition salts, wherein $R^1$ denotes the radical $R^3(R^4)N-$,

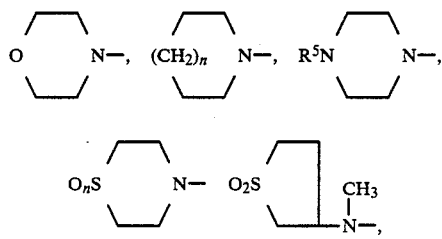

$R^2$ denotes the radical 1-methoxyethyl (—CH(CH$_3$)OCH$_3$), acetoxyphenyl-methyl (—CH(C$_6$H$_5$)O—COCH$_3$), 1-(ethoxycarbonyl)-ethoxy (—O—CH(CH$_3$)CO$_2$C$_2$H$_5$), 3-p-menthyloxy, 3-pinanyloxy, 2-bornyloxy, 2-methyl-butoxy (—O—CH$_2$CH(CH$_3$)-CH$_2$CH$_3$) or 2,2-dimethyldioxolan-4-yl-methoxy, or a radical of the formula II or IIa

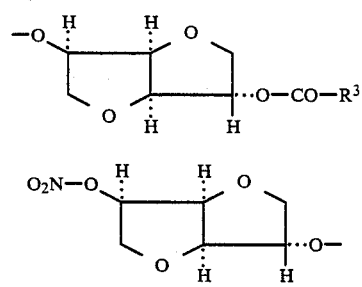

$R^3$ and $R^4$ denote alkyl($C_1$-$C_4$), $R^5$ denotes alkyl(-$C_1$-$C_4$), $R^3$—SO$_2$—, $R^3$O—CO— or ($R^3$)($R^4$)N—SO$_2$— and n denotes 0, 1 or 2.

The invention furthermore relates to a process for the preparation of the compounds of the formula I, their use and pharmaceutical products containing them.

The alkyl radicals represented by $R^3$, $R^4$ and $R^5$ can be straight-chain or branched.

The radicals represented by $R^2$ all contain at least one asymmetric carbon atom. The compounds of the formula I therefore exist in optically active (R) or (S) form ((R)="rectus", (S)="sinister").

Preferred radicals $R^1$ are morpholino, 4-methylsulphonylpiperazinyl, 4-ethoxycarbonyl-piperazinyl and 4-dimethylaminosulphonyl-piperazinyl.

The radical represented by $R^2$ in the formula II is derived from a 2—O—(CO—$R^3$)-isosorbide of the formula IIb

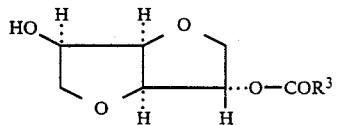  (IIb)

and the radical represented by $R^2$ in the formula IIa is derived from isosorbide 5-nitrate of the formula IIc

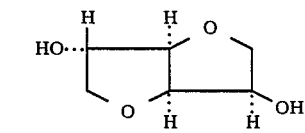  (IIc)

The compound which has a —H in the formula IIb instead of the —CO—$R^3$ radical and the compound which has a —H in the formula IIc instead of the —NO$_2$ radical has the formula IId

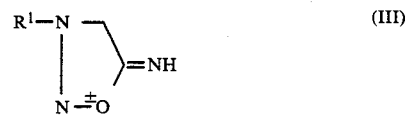  (IId)

It is called, for example, isosorbide, 1,4: 3,6-dianhydro-D-glucitol or 1,4: 3,6-dianhydro-D-sorbitol. In the context of the present invention, for reasons of simplification, the optically active radical of the formula II is called 2-alkanoylisosorbid-oxy and the optically active radical of the formula IIa is called 5-nitro-isosorbid-oxy.

The substituted 3-aminosydnonimines of the formula I are prepared by acylation of 3-aminosydnonimines of the formula III $R^1$—N... =NH ... (III)

or salts thereof, with acylating agents which introduce the acyl radical $R^2$—CO—. In this acylation, a hydrogen atom of the imino group of the compound III is replaced by the radical $R^2$—CO—. Examples of suitable acylating agents are compounds of the formula IV $R^2$—CO—X   (IV)

wherein $R^2$ has the meaning already given and X denotes halogen, in particular —Cl or —Br, —OH, —O—alkyl, in particular with 1 to 5 C atoms, —O—CO—$R^2$ or —O—CO—O—alkyl, in particular with 1 to 5 C atoms in the alkyl radical, —O—aryl, —O—nitroaryl or —O—dinitroaryl, in particular phenoxy, 2- or 4-nitrophenoxy or 2,4-dinitrophenoxy, —OCH$_2$CN or the radical of an azole or benzazole which has at least 2N atoms in the quasi-aromatic five-membered ring and is bonded via an N atom.

The acylating agents of the formula IV are thus, for example, carboxylic acid halides, in particular carboxylic acid chlorides and carboxylic acid bromides, of which the carboxylic acid chlorides are preferred, carboxylic acids, carboxylic acid esters, carboxylic acid anhydrides or mixtures of carboxylic acid/carbonic acid anhydrides or heterocyclic amides or azolides.

The acylating agents of the formula IV wherein X has the meaning given, with the exception of —OH, do not absolutely have to be employed in the pure form in the acylation, but they can also be produced shortly before the acylation reaction or during the acylation reaction in situ from the carboxylic acids of the formula IVa $$R^2\text{---CO---OH} \tag{IVa}$$

that is to say, the carboxylic acids of the formula IVa can also be used as acylating agents.

If the carboxylic acids of the formula IVa are used as acylating agents, it is advantageous to add an activating agent, which has the task of increasing or activating the acylating potential of the carboxylic acid. Examples of suitable activating agents of this type are: (a) dehydrating or water-binding agents and (b) those agents which are capable of converting the carboxylic acids of the formula IVa into the corresponding acid halides, anhydrides, esters, mixed carboxylic acid/carbonic acid anhydrides or azolides which act as acylating agents.

Possible suitable water-binding or dehydrating agents are, for example, N,N'-disubstituted carbo-diimides of the formula V $$R'\text{---N}{=}\text{C}{=}\text{N---R}'' \tag{V}$$

wherein R' and R" represent aliphatic, cycloaliphatic, araliphatic, aromatic or heteroaromatic radicals, especially if the radical R' and, if appropriate, also the radical R" is a secondary or tertiary alkyl radical (compare Methodicum Chimicum, Verlag G. Thieme Stuttgart, Volume 6, (1974) page 682). Examples of suitable carbo-diimides are di-isopropyl-, di-cyclohexyl- or methyl-tert.butyl-carbo-diimide. In carrying out the acylation reaction, the compound of the formula III and the carboxylic acid of the formula IVa and the carbo-diimide are then brought together in a suitable inert solvent or diluent, the desired acylation product of the formula I and, from the carbo-diimide, the corresponding disubstituted urea being formed.

Examples of agents which can convert the carboxylic acids of the formula IVa into the corresponding halides, carboxylic acid esters, anhydrides, mixed carboxylic/-carbonic acid anhydrides or azolides are, above all, carbonic acid derivatives, such as, for example, phosgene Cl—CO—Cl, chloroformic acid esters Cl—CO—O-alkyl, in particular with 1 to 5 C atoms in the alkyl radical (compare, for example, Tetrahedron Letters 24 (1983) 3365), carbonic acid esters R'''—O—CO—O—R'''', wherein R''' and R'''' represent aromatic or heteroaromatic radicals or radicals, bonded via the N atom, of cyclic acid imides of aliphatic or aromatic carboxylic acids, such as, for example, N,N'-disuccinimido-carbonate, diphthalimidocarbonate, 1,1'-(carbonyldioxy)-di-(benzo-triazole) or di-2-pyridyl carbonate (compare, for example, Tetrahedron Letters, Volume 25, No. 43, 4943–4946), if appropriate in the presence of suitable catalysts, such as, for example, 4-dimethylaminopyridine, or heterocyclic diamides of the carbonic acid of the formula A—CO—A, wherein A denotes a radical of an azole which has at least 2 nitrogen atoms in the quasi-aromatic five-membered ring and is bonded via an N atom. Examples of suitable heterocyclic diamides of this type are N,N'-carbonyl-diimidazole, 2,2'-carbonyl-di-1,2,3-triazole, 1,1'-carbonyl-di-1,2,4-triazole, N,N'-carbonyldipyrazole, 2,2'-carbonyl-ditetrazole, N,N'-carbonyl-benzimidazole or N,N'-carbonylbenztriazole. These compounds are in general combined before the actual acylation of the compound III with the carboxylic acid of the formula IVa in a suitable solvent or dispersing agent in stoichiometric ratios at temperatures from 0° C. up to the boiling point of the solvent or diluent, usually at 10° to 100° C., preferably 20° to 80° C., the azolide of the formula $$R^2\text{---CO---A}$$

wherein $R^2$ and A have the meanings already given, which acts as the actual acylating agent being formed in a few minutes. This can then be used immediately in the same pot for acylation of the 3-aminosydnonimine of the formula III (compare, for example, H. A. Staab, M. Lücking and F. H. Dürr, Chem. Ber. 95, (1962), 1275, and H. A. Staab and W. Rohr "Synthesen mit heterocyclischen Amiden (Azoliden)" in "Neuere Methoden der Praparativen Organischen Chemie" ("Syntheses with heterocyclic amides (azolides)" in "Recent Methods of Preparative Organic Chemistry"), Volume V, Verlag Chemie, 1967, page 53 et seq., in particular page 68). Commercially available N,N'-carbonyl-diimidazole is frequently used as the N,N'-carbonyl-diazole. However, the other N,N'-carbonylazoles are likewise readily accessible from the particular azole and phosgene.

Instead of the carbonic acid derivatives, the corresponding derivatives of oxalic acid, such as, for example, oxalyl chloride Cl—CO—CO—Cl (compare, for example, British Patent Specification 2,139,725) or N,N-oxalyl-diazoles A—CO—CO—A, wherein A has the meaning already given (compare, for example, Bull. Chem. Soc. Jap. 57, 3597–3598 (1984)) can frequently also be employed as the activating agent for the carboxylic acids of the formula IVa.

However, other compounds, such as, for example, methylethylphosphinic acid anhydride (compare, for example, German Offenlegungsschrift 3,101,427), are also suitable as activating agents for the carboxylic acids IVa.

The reaction between the acylating agent and the compound III is advantageously carried out in the liquid phase in the presence of an inert solvent, dispersing agent or diluent.

Examples of suitable solvents, dispersing agents or diluents are alcohols, in particular those with 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example, diethyl ether, methyl ethyl ether, di-n-propyl ether, di-isopropyl ether, methyl n-butyl ether, ethyl propyl ether, di-butyl ether, tetrahydrofuran, 1,4-dioxane, 1,2-dimethoxyethane and bis-β-methoxyethyl ether; polyethers, such as, for example, polyethylene glycols with a molecular weight of up to about 600; oligoethylene glycol dimethyl ethers, such as, for example, pentaglymes; crown ethers, that is to say cyclic polymers of ethylene glycol of the formula (—OCH$_2$CH$_2$)$_p$, wherein p is a number, for example, from 4 to 10 and it also being possible for one or more benzene rings to be fused onto the ring; aza- and thia-crown ethers (coronand-amines and coronand-sulphides); glycols and partly etherified glycols, such as, for example, ethylene glycol, propylene glycol, trimethylene glycol, ethylene glycol monomethyl ether, ethylene glycol monoethyl ether and diethylene glycol monoethyl ether; aliphatic hydrocarbons, such as, for example, benzines and low- and high-boiling petroleum ethers; aromatic hydrocarbons, such as, for example, benzene, toluene, o-, m- and p-xylene and pyridine; halogenated aliphatic or aromatic hydrocarbons, such as, for example, methylene chloride, chloroform, carbon tetrachloride, ethylene chloride, chlorobenzene and dichlorobenzene; nitriles, such as, for example, acetonitrile; amides, such as, for example, dimethylformamide or N-methyl-pyrrolidone; sulphoxides, such as, for example, dimethyl sulphoxide; and water. Mixtures of various solvents, dispersing agents or diluents can also be used, for example water/methylene chloride and water/toluene. An excess of the acylating agent can also be used as the solvent, dispersing agent or diluent.

The alcohols, glycols and partly etherified glycols and water mentioned as solvents, dispersing agents or diluents are usually suitable only for the acylation with carboxylic acid esters, whilst they are not sufficiently inert and are therefore less suitable for carrying out the acylation with other acylating agents because of the competing formation of esters, glycol esters or acids.

The molar ratio between the compound of the formula III and the acylating agent is 1:1. The acylating agent is advantageously employed in a slight molar excess. Excesses of up to 30 mol % are as a rule sufficient, that is to say the molar ratio between the compound of the formula III and the acylating agent of the formula IV is usually 1: (1 to 1.3), preferably 1: (1 to 1.2). If an acid is split off in the acylation reaction, it is advantageous to add an acid-trapping agent, such as, for example, an alkali metal hydroxide, such as, for example, sodium hydroxide, potassium hydroxide or lithium hydroxide, a tertiary organic amine, such as, for example, pyridine or triethylamine, an alkali metal carbonate or alkali metal bicarbonate, such as, for example, sodium carbonate or sodium bicarbonate, or an alkali metal salt of a weak organic acid, such as, for example, sodium acetate. Suitable catalysts, such as, for example, 4-dimethylaminopyridine, can also be added for the acylation reaction.

The reaction between the acylating agent and the compound III can in principle be carried out at temperatures between −10° C. and the boiling point of the solvent, dispersing agent or diluent used. In many cases, the reaction is carried out at 0° to 50° C., in particular at 0° to 30° C. and preferably at room temperature.

The carboxylic acid derivatives employed as acylating agents have at least one centre of asymmetry. In the case of acylation with enantiomerically pure or optically active acylating agents of the formula IV, the optically active compounds of the formula I are obtained directly. This process is preferred. In the case of acylation with acylating agents of the formula IV which are racemates, racemates are initially obtained, and can be resolved into the optically active compounds of the formula I in a manner which is known per se, for example by conversion into diastereomeric salts.

The substituted 3-amino-sydnonimines of the general formula I according to the invention form acid addition salts with inorganic or organic acids. Inorganic or organic acids are suitable for the formation of such acid addition salts. Examples of suitable acids are hydrogen chloride, hydrogen bromide, naphthalenedisulphonic acid, in particular 1,5-naphthalenedisulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts can be prepared in the customary manner by combining the components, advantageously in a suitable solvent or diluent. If the acid addition salts are obtained in the synthesis of the compounds of the formula I, the free compounds of the general formula I can, if desired, be obtained from the acid addition salts in a known manner, for example by dissolving or suspending in water or rendering alkaline, for example with sodium hydroxide solution, and subsequent isolation.

The starting compounds of the general formula III required are known (compare, for example, Chem. Pharm. Bull. 19, 72–79 (1971); European Patent 59,356 and European Patent 23,343), or they can be prepared by methods which are known per se.

The acylating agents of the formula IV or IVa are also known and can be prepared by the methods known for the particular class of subatance.

The compounds of the general formula I and their pharmacologically acceptable acid addition salts have useful pharmacological properties.

Their action on the cardiovascular system is particularly pronounced. For example, they reduce blood pressure and also the pulmonary arterial pressure and the left ventricular enddiastolic pressure, and thus contribute to relief of cardiac activity in the sense of an antianginal action, without thereby provoking reflectory tachycardia. Compared with compounds of similar structure, in particular in comparison with the commercially available compound molsidomine (=3-morpholino-N-ethoxycarbonyl-sydnonimine) and the compounds according to European Patent Specification Nos. 0,023,343 and 0,059,356, they have, above all, a significantly longer action, which is of great importance for administration and compliance.

The compounds of the formula I and their pharmacologically acceptable acid addition salts can therefore be administered to humans as medicines by themselves, in mixtures with one another or in the form of pharmaceutical formulations which allow enteral or parenteral use and which contain, as the active constituent, an effective dose of at least one compound of the formula I or of an acid addition salt thereof, alongside customary pharmaceutically acceptable excipients and additives. The formulations normally contain about 0.5 to 90% by weight of the therapeutically active compound.

The medicines can be administered orally, for example in the form of pills, tablets, lacquered tablets, coated tablets, hard and soft gelatine capsules, solutions, syrups, emulsions or suspensions or aerosol mixtures. Administration can also be, however, rectal, for example in the form of suppositories, or parenteral, for example in the form of injection solutions, or percutaneous, for example in the form of ointments or tinctures.

Pharmaceutically inert inorganic or organic excipients can be used to prepare the pharmaceutical products. To prepare pills, tablets, coated tablets and hard gelatine capsules, it is possible to use, for example, lactose, maize starch or derivatives thereof, talc, stearic acid or salts thereof and the like. Excipients for soft gelatine capsules and suppositories are, for example, fats, waxes, semi-solid and liquid polyols, natural or hardened oils and the like. Suitable excipients for the preparation of solutions and syrups are, for example, water, sucrose, invert sugar, glucose, polyols and the like. Suitable excipients for the preparation of injection solutions are, for example, water, alcohols, glycerol, polyols, vegetable oils and the like.

In addition to the active compounds and excipients, the pharmaceutical products can also contain additives, such as, for example, fillers, extenders, disintegrating agents, binders, lubricants, wetting agents, stabilizers, emulsifiers, preservatives, sweeteners, colouring agents, flavouring agents, aromatizing agents, thickeners or diluents, buffer substances and furthermore solvents or solubilizing agents or agents for achieving a depot effect, as well as salts for modifying the osmotic pressure, coating agents or antioxidants. They can also contain two or more compounds of the formula I and/or their pharmacologically acceptable acid addition salts, and furthermore other therapeutically active substances.

Such further therapeutically active substances are, for example: β-receptor blockers, such as, for example, propranolol, pindolol or metoprolol; vasodilators, such as, for example, carbochomen, and antianginal agents, such as, for example, carbochromen or molsidomine; tranquilizers, such as, for example, ituric acid barb-derivatives, 1,4-benzodiazepines and meprobamate; diuretics, such as, for example, chlorothiazide; agents which tonicize the heart, such as, for example, digitalis products; hypotensive agents, such as, for example, hydralazine, dihydralazine and prazosin; clonidine, Rauwolfia alkaloids; agents which reduce the level of fatty acids in the blood, such as, for example, bezafibrate and fenofibrate; and agents for prophylaxis of thrombosis, such as, for example, phenprocoumon.

The compounds of the formula I, their pharmacologically acceptable acid addition salts and pharmaceutical products which contain the conpounds of the formula I or their pharmacologically acceptable acid addition salts as the active compound can be used on humans for combating or preventing diseases, for example as antihypertensive medicines for various forms of high blood pressure, in combating or preventing angina pectoris and the like, and in the treatment of disturbances in cerebral and peripheral circulation. The dosage can be varied within wide limits and is to be adjusted to suit the individual circumstances in each individual case. In general, a daily dose of about 0.01 to 10 mg/kg, preferably 0.05 to 5 mg/kg, of body weight is appropriate for oral administration in order to achieve effective results. In the case of intravenous administration, the daily dose is in general about 0.001 to 10 mg/kg, preferably 0.01 to 5 mg/kg, of body weight. The daily dose is usually divided into several, for example, 2, 3 or 4, part administrations, especially where relatively large amounts are administered. If appropriate, it may also be necessary, depending on the individual behaviour, to deviate upwards or downwards in the stated daily dose.

The value $\alpha_D^{20}$ stated in the following examples is the specific optical rotation of the substance for polarized light of the sodium D line (589 nm) at 20° C. In the examples, the solvent and concentration c in g/100 ml used in the measurement are stated in parentheses after the value stated for the specific optical rotation. If the corresponding data are missing, the measurements have been carried out in methanol at a concentration of 5.0 g in 100 ml of solution.

EXAMPLE 1

(a) 2-Methyl-butyl (S)-(—)-chloroformate 50 g of phosgene are dissolved in 250 ml of methylene chloride, with thorough cooling. 22 g of S-(—)-2-methyl-1-butanol are added dropwise to this cold solution. The solution is then allowed to reach room temperature and is subsequently stirred overnight and concentrated, and the residue is distilled in vacuo.

Yield: 32.6 g; boiling point$_{20\ mbar}$=56 to 58° C.

(b) (S)-(+)-N-(2-Methyl-butoxycarbonyl)-3-(4-methylsulphonyl-piperazin-1-yl)-sydnonimine 5 g of 3-(4-methylsulphonyl-piperazin-1-yl)-sydnonimine hydrochloride are suspended in 25 ml of H$_2$O and the suspension is cooled to 5° C. 3.2 g of sodium bicarbonate are added and a solution of 3 g of 2-methyl-butyl (S)-chloroformate in 25 ml of methylene chloride is rapidly added dropwise, with simultaneous stirring. The mixture is subsequently stirred for 6 hours, during which it is allowed to warm to room temperature. The methylene chloride phase is then separated off, dried over Na$_2$SO$_4$ and concentrated. The residue is recrystallized from ethanol.

Yield: 5.1 g; melting point=113 to 115° C.; $\alpha_D^{20}$=+4.0°

EXAMPLE 2

(a) Ethyl (S)-(—)-O-methyl-lactate 70 g of ethyl (S)-lactate and 100 g of methyl iodide are dissolved in 600 ml of tetrahydrofuran and the solution is cooled to 5° C. 24 g of sodium hydride (60% dispersion) are introduced in portions. The mixture is then subsequently stirred for one day, during which the mixture reaches room temperature. The sodium iodide which has precipitated out is filtered off with suction and the filtrate is washed twice with saturated sodium chloride solution, dried and concentrated. The residue is distilled in vacuo.

Yield: 59.6 g; boiling point$_{20\ mbar}$=41 to 42° C.; $\alpha_D^{20}$=—70° (without a solvent, in bulk, c=100)

(b) (S)-O-Methyl-lactic acid chloride 12.8 g of sodium are dissolved in 250 ml of ethanol. 7.2 ml of water and 52.8 g of ethyl (S)-(—)-O-methyl-lactate are added to this solution and the mixture is boiled under reflux for 1 hour. The mixture is then concentrated, the residue is stirred with ether and the solid is filtered off with suction and dried in vacuo. The solid is introduced into a solution of 50 ml of thionyl chloride in 100 ml of ether. After subsequently stirring the mixture overnight, it is filtered with suction, the filtrate is concentrated and the residue is distilled in vacuo.

Yield: 29 g; boiling point$_{67\ mbar}$=45 to 46° C.

(c) (S)-(—)-N-(1-Methoxypropionyl)-3-(4-ethoxycarbonyl)-piperazin-1-yl)-sydnonimine 6.9 g of 3-(4-ethoxycarbonyl-piperazin-1-yl)-sydnonimine hydrochloride are suspended in 25 ml of water and the suspension is cooled to 0° C. 4.5 g of sodium bicarbonate and a solution of 3.4 g of (S)-O-methyl-lactic acid chloride in 25 ml of methylene chloride are added. After the mixture has been subsequently stirred for four hours, the methylene chloride phase is separated, dried and concentrated. The residue is triturated with ether and filtered off with suction.

Yield: 5.2 g; melting point=92° to 94° C.; $\alpha_D^{20} = -18.4°$ (methanol, c=4.9)

The following compounds can be prepared analogously to Examples 1 and 2:

3. Starting from (+)-3-menthol:
   (+)-N-(3-p-methyl)-oxycarbonyl-3-(4-methylsulphonyl-piperazin-1-yl)-sydnonimine
   melting point=122° to 125° C.; $\alpha_D^{20} = +56.1°$ 4. Starting from (−)-3-pinanol:
   (−)-N-(3-pinanoyl)-oxycarbonyl-3-(4-methylsulphonyl-piperazin-1-yl)-sydnonimine
   melting point =105° to 109° C.; $\alpha_D^{20} = -37.4°$ (CH$_2$CL$_2$, c=2.7)

5. (S)-(+)-N-(2-Methyl-butoxycarbonyl)-3-morpholino-sydnonimine
   melting point=102° to 103° C.; $\alpha_D^{20} = +9.0°$ 6. Starting from ethyl (S)-lactate:
   (S)-(−)-N-(1-Ethoxycarbonyl)-ethoxycarbonyl-3-morpholino-sydnonimine
   melting point =77° to 78° C.; $\alpha_D^{20} = -52°$ 7. (+)-N-(3-p-Menthyl)-oxycarbonyl-3-morpholino-sydnonimine:
   melting point=149° to 150° C.; $\alpha_D^{20} = +64°$ 8. (−)-N-(3-p-Menthyl)-oxycarbonyl-3-morpholino-sydnonimine:
   melting point=150° to 151° C.; $\alpha_D^{20} = -60°$ 9. Starting from L(−)-borneol:
   (−)-N-(2-Bornyl)-oxycarbonyl-3-morpholino-sydnonimine
   melting point=137° to 138° C.; $\alpha_D^{20} = -30°$ 10. (−)-N-(3-Pinanyl)-oxycarbonyl-3-morpholino-sydnonimine:
    melting point=153° to 155° C.; $\alpha_D^{20} = -10.0°$ 11. Starting from (S)-2,2-dimethyl-4-hydroxymethyl-dioxolane:
    (R)-(+)-N-((2,2-dimethyldioxolan-4-yl)-methoxycarbonyl)-3-morpholino-sydnonimine
    melting point=113° to 114° C.; $\alpha_D^{20} = +4°$ 12. Starting from isosorbide 5-nitrate:
    (+)-N-(5-Nitro-isosorbid-oxycarbonyl)-3-morpholino-sydnonimine
    melting point=144° to 146° C.; $\alpha_D^{20} = +100°$ 13. Starting from isosorbide 2-acetate:
    (+)-N-(2-Acetyl-isosorbid-oxycarbonyl)-3-morpholino-sydnonimine
    melting point=163° C. (decomposition); $\alpha_D^{20} = +144°$ 14. (S)-(+)-N-(2-Methyl-butoxycarbonyl)-3-(4-ethoxycarbonyl-piperazin-1-yl)-sydnonimine:
    melting point=116° to 117° C.; $\alpha_D^{20} = +8°$ 15. (S)-(−)-(1-Ethoxycarbonyl)-ethoxycarbonyl)-3-(4-ethoxycarbonyl-piperazin-1-yl)-sydnonimine:
    melting point=98° to 100° C.; $\alpha_D^{20} = -40°$ 16. (−)-N-(3-p-Menthyl)-oxycarbonyl-3-(4-ethoxycarbonyl-piperazin-1-yl)-sydnonimine:
    melting point=145° to 147° C.; $\alpha_D^{20} = -56.2°$ 17. (+)-N-(3-p-Menthyl)-oxycarbonyl-3-(4-ethoxycarbonyl-piperazin-1-yl)-sydnonimine:
    melting point=146° to 147° C.; $\alpha_D^{20} = +57°$ 18. (−)-N-(3-Pinanyl)-oxycarbonyl-3-(4-ethoxycarbonyl-piperazin-1-yl)-sydnonimine:
    melting point=121° to 123° C.; $\alpha_D^{20} = -6°$ 19. (−)-N-(2-Bornyl)-oxycarbonyl-3-(4-ethoxycarbonyl-piperazin-1-yl)-sydnonimine:
    melting point=148° to 149° C.; $\alpha_D^{20} = -23°$ 20. (R)-(+)-N-((2,2-Dimethyldioxolan-4-yl)-methoxycarbonyl)-3-(4-ethoxycarbonyl-piperazin-1-yl)-sydnonimine:
    melting point=90° to 92° C.; $\alpha_D^{20} = +4°$ 21. (+)-N-(2-Acetyl-isosorbid-oxycarbonyl)-3-(4-ethoxycarbonyl-piperazin-1-yl)-sydnonimine:
    melting point=127° to 129° C.; $\alpha_D^{20} = +120°$ 22. Starting from (R)-O-methyl-lactic acid chloride:
    (R)-(+)-N-(1-methoxypropionyl)-3-(4-ethoxycarbonyl-piperazin-1-yl)-sydnonimine
    melting point=91° to 93° C.; $\alpha_D^{20} = +16.5°$ 23. (R)-(+)-N-(1-Methoxypropionyl)-3-(4-methylsulphonyl-piperazin-1-yl)-sydnonimine:
    melting point=187° to 188° C.; $\alpha_D^{20} = +47.0°$ 24. (S)-(−)-N-(1-Methoxypropionyl)-3-(4-methylsulphonyl-piperazin-1-yl)-sydnonimine
    melting point=185° to 187° C.; $\alpha_D^{20} = +46.7°$ 25. (S)-(−)-N-(1-Methoxypropionyl)-3-morpholino-sydnonimine
    melting point=121° to 123° C.; $\alpha_D^{20} = -18.03$ 26. Starting from (R)-(+)-acetyl-mandelic acid chloride:
    (R)-(+)-N-(1-acetoxy-phenylacetyl)-3-morpholino-sydnonimine
    melting point=110° to 144° C.; $\alpha_D^{20} = +106°$ 27. Starting from (S)-(−)-O-acetyl-mandelic acid chloride:
    (S)-(−)-N-(1-acetoxy-phenylacetyl)-3-morpholino-sydnonimine
    melting point=110° to 112° C.; $\alpha_D^{20} = -110°$ 28. (R)-(+)-N-(1-Acetoxy-phenylacetyl)-3-(4-ethoxycarbonyl-piperazin-1-yl)-sydnonimine
    melting point=85° C. (decomposition); $\alpha_D^{20} = +61.1°$ 29. (S)-(−)-N-(1-Acetoxy-phenylacetyl)-3-(4-ethoxycarbonyl-piperazin-1-yl)-sydnonimine:
    melting point=89° C. (decomposition); $\alpha_D^{20} = -76°$ 30. (R)-(+)-N-(1-Methoxypropionyl)-3-morpholino-sydnonimine
    melting point=122° to 124° C.; $\alpha_D^{20} = +14.1°$ 31. (−)-(2-Bornyl)-oxycarbonyl-3-(N-methyl-N-(sulpholan-3-yl-1,1-dioxo)-amino-sydnonimine
    melting point=157° C. (decomposition); $\alpha_D^{20} = -20°$ 32. (−)-N-(3-p-Menthyl-oxycarbonyl)-3-dimethylamino-sydnonimine:
    melting point=166° decomposition; $\alpha_D^{20} = -68.75°$ (methanol, c=2.4)

33. (−)-N-(3-p-Menthyl-oxycarbonyl)-3-piperidino-sydnonimine:
    melting point=121° to 123° C.; $\alpha_D^{20} = -80°$ (CH$_2$Cl$_2$, c=2.0)

34. (S)-(+)-N-(2-Methyl-butoxycarbonyl)-3-dimethylamino-sydnonimine hydrochloride:
    melting point 157° to 159° C.; $\alpha_D^{20} = +5.7°$ (H$_2$O, c=3.5)

35. (S)-(+)-N-(2-Methyl-butoxycarbonyl)-3-piperidino-sydnonimine:
    melting point=97° to 98° C.; $\alpha_D^{20} = +8.3°$ (CH$_2$Cl$_2$, c=3.0)

The following examples relate to pharmaceutical formulations:

|  | per tablet |
|---|---|
| Example A Tablets | |
| Active compound | 20 mg |
| Lactose | 60 mg |

|  | per tablet |
|---|---|
| Maize starch | 30 mg |
| Soluble starch | 5 mg |
| Magnesium stearate | 5 mg |
|  | 120 mg |
| Example B | |
| Coated tablets | |
| Active compound | 6 mg |
| Propanolol | 40 mg |
| Lactose | 90 mg |
| Maize starch | 90 mg |
| Secondary calcium phosphate | 34 mg |
|  | 260 mg |
| Example C | |
| Capsules | |
| Active compound | 5 mg |
| Prazosin | 5 mg |
| Maize starch | 185 mg |
|  | 195 mg |
| Example D | |
| Injection solution | |
| Active compound | 4 mg |
| Sodium chloride | 0.7 mg |
| Water for injection purposes to | 1 ml |
| Example E | |
| Suppositories | |
| Active compound | 20 mg |
| Suppository base to | 2 g |

The pharmacological efficacy of the compounds of the invention was tested using the following method: Mongrel dogs of either sex weighing 15–25 kg were used. After i.v.-pretreatment with 22 mg piritramid (Dipidolor ®) the dogs were anesthetized with sodium pentobarbiral 30 mg/kg i.v. and artificially ventilated. A fluid-filled Tygon-catheter (diameter 1.0×1.78 mm) was implanted into the abdominal aorta via the superficial circumflex iliac artery for blood pressure measurement. A left side thoracotomy was performed at the 5th intercostal space and a thick walled tygon-catheter (diameter 0.76×2.28 mm) was implanted into the left ventricle for measurement of left ventricular pressure and contractility (LVP, LVEDP, dp/dt max). Hypertension was induced by placing constrictors around renal arteries of both side.

Hemodynamics measurements were made not earlier than a fortnight after surgery.

The test compounds were administered orally in a dose of 0.2 mg/kg.

The data obtained are apparent from the following table:

TABLE

| Compound according to Example | Δ BP s/d (mm Hg) | | Δ LVEDP (mm Hg) | | Δ HR (b/min) | Δ dp/dt (mm Hg/s) |
|---|---|---|---|---|---|---|
| 1 | −50/−10 | >300' | −4 | 240' | +25 | −300 |
| 2 | −40/−10 | 240' | −6 | 240' | +30 | −250 |
| 4 | −30/−10 | 180' | −6 | 180' | +5 | 0 |
| 6 | −40/−30 | 210' | −5 | 210' | +5 | 0 |
| 7 | −20/−10 | 240' | −4 | 90' | +20 | +200 |
| 8 | −20/−10 | 240' | −4 | 240' | +20 | −200 |
| 10 | −15/−5 | 120' | −5 | 240' | −10 | −200 |
| 11 | −50/−15 | 360' | −7 | 360' | +40 | 0 |
| 12 | −35/−5 | 300' | −6 | 300' | +25 | +200 |
| 14 | −50/−15 | 300' | −6 | 200' | +30 | −200 |
| 16 | −25/0 | 180' | −3 | 180' | 0 | −150 |
| 25 | −40/−10 | 300' | −8 | 240' | +30 | +300 |
| 28 | −50/−10 | 240' | −7 | 180' | +30 | −400 |
| 29 | −30/−5 | 180' | −5 | 180' | +30 | −300 |
| 30 | −40/−10 | >240' | −5 | 180' | +30 | −500 |
| 31 | −25/−5 | 360' | −5 | 300' | +35 | −200 |
| 34 | −40/−10 | 360' | −7 | 360' | +20 | −200 |
| 35 | −30/−10 | 180' | −7 | 180' | +30 | +200 |
| Molsidomine (Comparison substance) | −35/−10 | 120' | −6 | 120' | +20 | −200 |

The data indicated in the columns of the preceding table have the following meanings:

(a) ΔBP s/d (mm Hg): Change in the systolic/diastolic blood pressure in mm Hg. The third value in that column refers to the duration of the effect in minutes.

(b) ΔLVEDP (mm Hg): Change in the left-ventricular enddiastolic pressure in mm Hg. The second value in that column indicates the duration of the effect in minutes.

(c) HR (b/min): Change in the heart rate in beats per minute.

(d) Δdp/dt (mm Hg/s): Change in the rate of the pressure rise in mm Hg per second.

We claim:

1. Substituted 3-aminosydnonimine of the general formula I

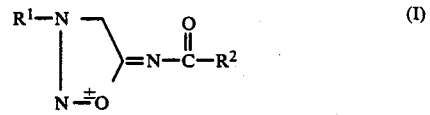

in optically active form, or a pharmaceutically acceptable acid addition salt thereof, wherein $R^1$ denotes the radical $R^3(R^4)N-$,

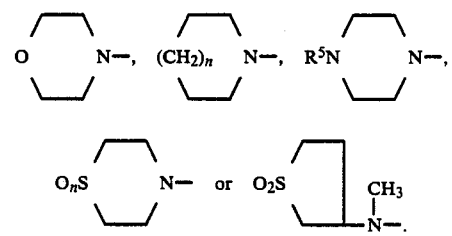

$R^2$ denotes the radical 1-methoxyethyl (—CH(CH$_3$)OCH$_3$), acetoxyphenyl-methyl (—CH(C$_6$H$_5$)O—COCH$_3$), 1-(ethoxycarbonyl)-ethoxy (—O—CH(CH₃)CO₂C₂H₅), 3-p-menthyloxy, 3-pinanyloxy, 2-bornyloxy, 2-methyl-butoxy (—O—CH₂CH(CH₃)—CH₂CH₃) or 2,2-dimethyl-dioxolan-4-yl-methoxy, or a radical of the formula II or IIa

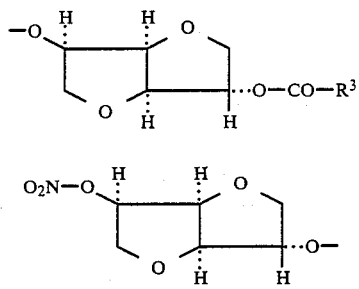

$R^3$ and $R^4$ denote alkyl($C_1$-$C_4$), $R^5$ denotes alkyl($C_1$-$C_4$), $R^3$—SO₂—, $R^3$O—CO— or ($R^3$)($R^4$)N—SO₂— and n denotes 0, 1 or 2.

2. Substituted 3-aminosydnonimine according to claim 1, characterized in that $R^1$ denotes the radical

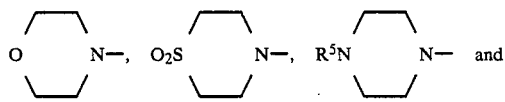

$R^5$ denotes CH₃—SO₂—, C₂H₅O₂C— or (CH₃)₂N—SO₂—.

3. (S)-(+)-N-(2-Methyl-butoxycarbonyl)-3-(4-methylsulphonyl-piperazin-1-yl)-sydnonimine.

4. (S)-(−)-N-(1-Methoxypropionyl)-3-(4-ethoxycarbonyl-piperazin-1-yl)-sydnonimine.

5. (R)-(+)-N-(2,2-Dimethyl-1,3-dioxolan-4-yl-methoxycarbonyl)-3-morpholino-sydnonimine.

6. A pharmaceutical composition useful for combating and/or preventing angina pectoris, high blood pressure, and/or disturbances of cerebral and peripheral blood flow and having, as active component, from about 0.5 to 90 percent by weight of a compound of claim 1 or of a pharmaceutically-acceptable acid-addition salt thereof, together with a pharmaceutically-acceptable vehicle and, optionally, a pharmaceutically-acceptable additive.

7. A Process for combating or preventing angina pectoris, high blood pressure, and disturbances of cerebral and peripheral blood flow which comprises administering an effective amount of a pharmaceutically-active substituted 3-aminosydnonimine of claim 1, or of a pharmaceutically-acceptable acid-addition salt thereof, to a host which is subject to or afflicted with one or more of these conditions.

8. A process for the treatment of cardiovascular disease which comprises administering an effective amount of a pharmaceutically-active substituted 3-aminosydnonimine as defined in claim 1 or a pharmaceutically-acceptable acid addition salt thereof to host in need thereof.

* * * * *